(12) United States Patent
Anderson et al.

(10) Patent No.: US 6,352,152 B1
(45) Date of Patent: Mar. 5, 2002

(54) METHOD AND PACKAGE FOR STORING A PRESSURIZED CONTAINER CONTAINING A DRUG

(75) Inventors: Gregor John McLennan Anderson; Karl Andrew Garrill, both of Hertford (GB); Richard J. Haan, Germantown, TN (US); Craig Steven Herman; Vincent P. Pisculli, both of Raleigh, NC (US); Richard Ian Walker, Hertford (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/599,702

(22) Filed: Jun. 20, 2000

Related U.S. Application Data

(63) Continuation-in-part of application No. 09/571,388, filed on May 15, 2000, which is a continuation-in-part of application No. 09/290,351, filed on Apr. 12, 1999, now Pat. No. 6,179,118, which is a continuation-in-part of application No. 09/216,183, filed on Dec. 18, 1998, now Pat. No. 6,119,853.

(51) Int. Cl.$^7$ .............................................. B65D 81/26
(52) U.S. Cl. ...................... 206/204; 206/438; 206/439; 206/497
(58) Field of Search ...................... 128/200.14, 200.21, 128/200.22, 200.23; 206/204, 438, 439, 497, 570; 383/113

(56) References Cited

U.S. PATENT DOCUMENTS

| 3,788,322 | A |   | 1/1974  | Michaels |
|-----------|---|---|---------|----------|
| 3,797,492 | A |   | 3/1974  | Place |
| 3,809,223 | A | * | 5/1974  | Kendall ...................... 206/204 |
| 4,135,622 | A |   | 1/1979  | Glick |
| 4,449,632 | A |   | 5/1984  | Marusiak, Jr. |
| 4,509,196 | A |   | 4/1985  | Sak et al. |
| 4,655,229 | A |   | 4/1987  | Sensabaugh, Jr. et al. |
| 4,702,963 | A |   | 10/1987 | Phillips et al. |
| 4,874,090 | A |   | 10/1989 | Dyke |
| 4,907,394 | A |   | 3/1990  | Tschepke et al. |
| 4,988,558 | A |   | 1/1991  | Shigemoto |
| 5,073,599 | A |   | 12/1991 | Genske |
| 5,201,308 | A | * | 4/1993  | Newhouse ............. 128/203.15 |
| 5,322,161 | A |   | 6/1994  | Shichman et al. |
| 5,441,060 | A |   | 8/1995  | Rose et al. |
| 5,472,092 | A | * | 12/1995 | Evert ......................... 206/497 |
| 5,522,385 | A | * | 6/1996  | Lloyd et al. ........... 128/200.14 |
| 5,524,613 | A | * | 6/1996  | Haber et al. ........... 128/203.15 |
| 5,551,557 | A | * | 9/1996  | Brooks ....................... 206/204 |
| 5,645,051 | A |   | 7/1997  | Schultz et al. |
| 5,687,746 | A |   | 11/1997 | Rose et al. |
| 5,718,355 | A |   | 2/1998  | Garby et al. |
| 5,746,227 | A |   | 5/1998  | Rose et al. |
| 5,756,171 | A |   | 5/1998  | Moteki et al. |
| 5,775,321 | A | * | 7/1998  | Alband ................... 128/200.23 |
| 5,833,066 | A |   | 10/1998 | Hargus et al. |
| 5,957,124 | A | * | 9/1999  | Lloyd et al. ........... 128/200.22 |
| 6,103,280 | A | * | 8/2000  | Molzahn et al. ............. 426/109 |

FOREIGN PATENT DOCUMENTS

| EP | 0 414 536 | 8/1990 |
| EP | 0 428 380 | 11/1990 |

* cited by examiner

Primary Examiner—Jim Foster
(74) Attorney, Agent, or Firm—Christopher P. Rogers

(57) ABSTRACT

A method and package for storing a pressurized container which is filled with a drug formulation at a predetermined pressure. The drug formulation includes a mixture of a drug and a propellant. The package which encloses the pressurized container substantially prevents ingression of water vapor and particulate matter into the package while permitting egression of the propellant which may leak from the pressurized container.

34 Claims, 4 Drawing Sheets

METHOD AND PACKAGE FOR STORING A PRESSURIZED CONTAINER CONTAINING A DRUG

CROSS REFERENCE TO RELATED APPLICATIONS

This application is a continuation-in-part of U.S. application Ser. No. 09/571,388, filed on May 15, 2000, which is a continuation-in-part of U.S. application Ser. No. 09/290, 351, filed on Apr. 12, 1999, now U.S. Pat. No. 6,179,118 the entire contents of both of which are incorporated by reference; and for which an international application PCT/US99/27851 was filed Nov. 23, 1999; and continuation-in-part of a U.S. application Ser. No. 09/216,183 filed Dec. 18, 1998 now U.S. Pat. No. 6,119,853.

BACKGROUND OF TH INVENTION

1. Field of the Invention

The present invention relates to a method and package for storing a pressurized container containing a drug.

2. Description of the Background Art

For environmental reasons, there has been a move to replace chlorofluorocarbons (CFCs) (also simply known as "fluorocarbons") such as P11, P114 and P12 with hydrofluoroalkane propellants such as HFA-134a and HFA-227. When these hydrofluoroalkane propellants are used as a propellant in a pressurized drug delivery system, various technical problems can occur with various drug formulations. Also, it is necessary to modify the construction of metered dose inhalers for optimum stability and aerosol formation.

One storing mechanism for a metered dose inhaler (MDI) uses a plastic tube which has a resealable lid to close the tube. The resealable lid for this tube employs a desiccant to absorb moisture present in the tube.

Such plastic tubes typically increase manufacturing cost and require complex and/or expensive manufacturing processes. Such tubes are frequently bulky in that they require a significant amount of storage space relative to the size of the container disposed within the plastic tube.

It is well established that non-CFC propellants, especially HFC 134a, have a much greater water solubility than the CFC propellants traditionally used in MDI's. The maximum water solubility in HFC 134a is about 2200 ppm whereas for CFC 11, 12 and 114, the maximum water solubilities are about 130 ppm. (See Pischtiak, A. (1999) "Solvay Fluor and Derivate Chemical Data Sheet for CFC and HFC Propellants.")

This maximum solubility may be further increased if cosolvents such as ethanol are used in the formulation. The mechanism of moisture transport into HFC MDI's has been discussed by Williams, G. and Tcherevatchenkoff, A. (1999) "Moisture Transport Into CFC-Free MDI's," Respiratory Drug Delivery VI, Hilton Head, S.C., USA.

They concluded that moisture transport is influenced by the elastomeric nature of the valve gaskets as well as the type of HFA formulation and storage conditions employed. It may be appropriate, under certain circumstances to control the ingress of moisture into HFC based MDI's. A good example of this would be with a hygroscopic drug substance. Hence, prevention of moisture ingress is the subject of this invention whereby a series of secondary packaging embodiments demonstrate advantageously reducing moisture ingress.

SUMMARY OF THE INVENTION

Accordingly, a need in the art exists for a method and package for storing a pressurized container filled with a propellant and a drug which substantially prevents ingression of water vapor and particulate matter into the storage package while permitting egression of the propellant to increase shelf life and performance of the drug and the propellant. Furthermore, a need exists in the art to provide a method and package for storing a pressurized container filled with a drug and a propellant which is cost effective and which does not require complex manufacturing processes and which in turn efficiently envelopes the container to maximize available storage space.

It is a primary object of the present invention to provide a method and package for storing a pressurized container, where the pressurized container is filled with a drug and a propellant and where the method and package substantially prevent ingression of water vapor and particulate matter into the package while permitting egression of the propellant whereby shelf life of the drug is prolonged and performance of the drug and the propellant are maintained or increased.

It is a further object of the present invention to provide a method and package for storing a pressurized container filled with a drug and a propellant where the method and package substantially absorb residual moisture in the package enclosing the pressurized container that is sometimes present on the outer surface of the pressurized container prior to sealing pressurized container within the package.

Another object of the present invention is to provide a method and package for storing a pressurized container including a drug and a propellant which substantially reduces manufacturing costs while substantially reducing the complexity of the manufacturing process of the package.

Another object of the present invention is to provide a method and package for storing a pressurized container having a drug and a propellant which is easily opened and readily disposable.

It is a further object of the present invention to provide a method and package for storing a pressurized container having a drug and a propellant, whereby the propellant preferably meets governmental guidelines which prohibit the use of CFCs.

Another object of the present invention is to provide a method and package for storing a pressurized container which includes a drug and a propellant that does not require complex mechanical devices to envelope or enclose the pressurized container while substantially reducing the amount of storage space needed for the pressurized container where the package substantially conforms to the shape of the pressurized container. The package is amorphous in shape due to the flexible materials from which it is made.

Another object of the present invention is to provide a method and package which form an enclosed volume that stores a pressurized container in a controlled environment where the pressurized container is isolated from harmful environmental conditions such as humidity, dust, light, and water vapor and other particulate matter.

Another object of the present invention is to provide and article of manufacture comprising an integral aerosol dispensing apparatus, a drug formulation, and a flexible package. It is further an object of the present invention to provide a drug formulation and carrier with packaging material having labeling and information relating to the composition contained therein and printed thereon. Additionally, a further object of the invention is to provide an article of manufacture having a brochure, report, notice, pamphlet, or leaflet containing product information.

These and other objects of the present invention are fulfilled by providing a container storage system comprising: a drug formulation comprising a mixture of a drug and a propellant; a pressurized container filled with the drug formulation at a predetermined pressure; and a flexible package for wrapping and sealing the pressurized container providing an enclosed volume in which the pressurized container is disposed, the flexible package being impermeable to water vapor and permeable to the propellant, the flexible package substantially preventing ingression of water vapor and particulate matter into the enclosed volume while permitting egression of the propellant.

In addition, these and other objects of the present invention are also accomplished by providing a method of storing a container comprising the steps of: providing a flexible package material, which is impermeable to water vapor and permeable to a propellant; filling a container with a drug formulation comprising a drug and the propellant at a predetermined pressure; wrapping the container with the flexible package material to form an enclosed volume in which the container is disposed therein; and sealing the flexible package which in turn closes said enclosed volume, the flexible package substantially preventing ingression of water vapor and particulate matter into the enclosed volume while permitting egression of the propellant from the enclosed volume.

Moreover, these and other objects of the present invention are fulfilled by a packaged metered dose inhaler comprising: an MDI comprising a container and a drug metering valve, a pressurized drug formulation in the container comprising a propellant and a drug dispersed or dissolved in the propellant; and an overwrap of flexible material enclosing said MDI, the overwrap being made of a moisture impermeable material.

Also, these and other objects of present invention are accomplished by providing an article of manufacture comprising: an aerosol dispensing apparatus for dispensing metered amounts of fluid material from a reservoir, the apparatus comprising a container defining a reservoir, a dispensing valve; a drug formulation located within the aerosol dispensing apparatus comprising a safe and effective medicament and a pharmaceutically acceptable propellant; and a flexible package for wrapping and sealing the container providing an enclosed volume in which said pressurized container is disposed, the flexible package being substantially impermeable to water vapor and permeable to the propellant, the flexible package substantially preventing ingression of water vapor and particulate matter into the enclosed volume while permitting egression of the propellant.

These and other objects of the present invention are also accomplished by providing a method of improving a product performance comprising the steps of: providing a flexible package material made of at least one heat sealable layer, at least one layer of a metal foil, and a protective layer; the flexible package material being impermeable to water vapor and permeable to a propellant; filling a container with a drug formulation comprising a drug and the propellant at a predetermined pressure; wrapping the container with the flexible package material to form an enclosed volume in which the container is disposed therein; and sealing the flexible package which in turn closes the enclosed volume, the flexible package substantially preventing ingression of water vapor and particulate matter into the enclosed volume while permitting egression of the propellant from the enclosed volume.

Another aspect of the invention includes a desiccant-containing, substantially moisture impermeable film that has been heat-shrinked onto portions of the metered dose inhaler. By "substantially moisture impermeable" it is meant that no more than insignificant or trace amounts of moisture may pass through the film. This invention is directed to an apparatus comprising a drug formulation comprising a mixture of at least a drug and an HFA propellant, a fluid dispensing device including a pressurized container filled with said drug formulation, and a substantially moisture-impermeable polymeric film heat-shrinked onto at least a portion of the exterior of the fluid dispensing device, wherein the polymeric film comprises a first moisture absorbing material. Preferably, the drug is albuterol sulfate and the propellant is HFA 134a. The fluid dispensing device may further include a valve having a stem. Preferably the film is heat-shrinked onto the pressurized container, the valve, and the region defined by the exterior interface of the valve and stem. Alternatively, the film may be heat-shrinked onto a portion of the pressurized container and a portion of the valve. The apparatus may further include a second moisture absorbing material located within the pressurized container. The first and second moisture absorbing material may be a desiccant such as nylon, silica gel, zeolite, alumina, bauxite, anhydrous calcium sulphate, activated bentonite clay, water absorbing clay, molecular sieve or combinations thereof. The second desiccant may be contained within a sachet constructed from nylon or loose within the pressurized container. The sachet may be fixedly attached to the pressurized container. The second desiccant may be in the form of granules or beads suitably large in size to avoid clogging a valve in the metered dose inhaler.

The polymeric film of the heat shrink wrap may be constructed from one or more polymeric layers. Preferably, the one or more polymeric layers of the polymeric film are each constructed from polyvinylchloride, polyvinylidenechloride, polypropylene, oriented polypropylene, polyethylene, ACLAR® or BAREX®. Preferably, individual or a combination of polymeric layers are oriented or otherwise modified so as to provide a customized shrinking. For example, the oriented polypropylene layer may be employed in such a manner so as to provide predominately greater shrinking around the valve/cannister interface, at the valve/stem interface and around the rest of the cannister (as opposed to along the length of the MDI) to provide enhanced sealing of the MDI to ambient moisture. Preferably, the polymeric film remains on the MDI during storage and throughout the useful life of the MDI to more advantageously (1) absorb any moisture located inside the MDI, and (2) seal off the MDI from ambient moisture. The polymeric film may further include one or more adhesive layers. The first moisture absorbing material may be a first desiccant. At least one of said polymeric layers may be impregnated, coated, treated or lined with said first desiccant. At least one of said adhesive layers may also be impregnated with the first desiccant. The desiccant may be incorporated with the polymeric or adhesive layer by conventional methods known in the art, such as by spray coating, blending prior to extrusion, or other suitable methods. Preferably, the substantially moisture-impermeable polymeric film is preformed or prefabricated. Such preforming or prefabrication may be performed by conventional methods such as by extruding the film layer, cutting to length and heat or chemical/mechanical sealing.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Pressurized Containers

Figure 1:
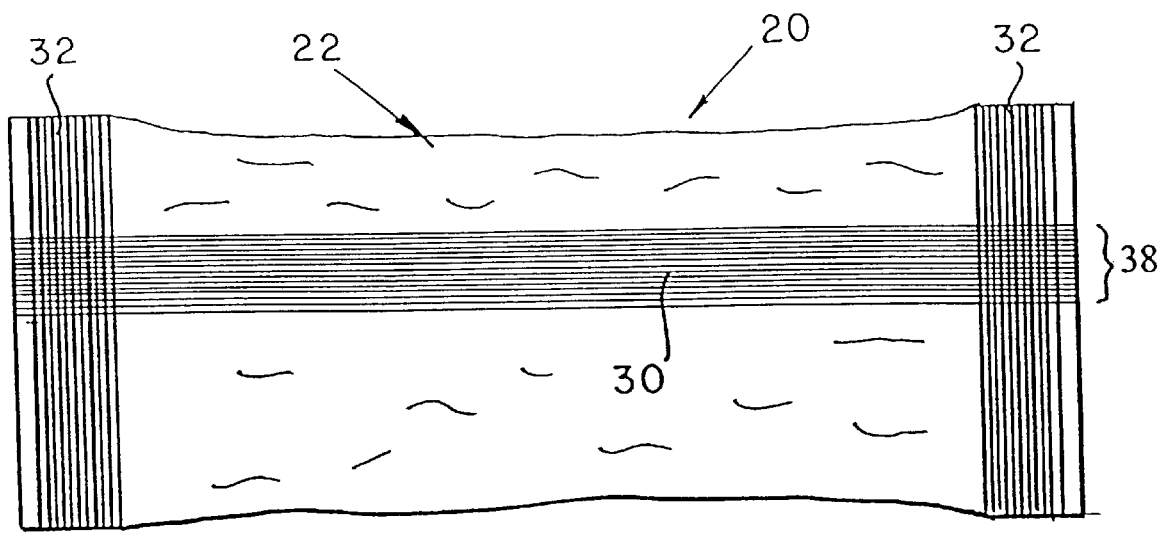
FIG. 1 is a top elevational view of the package for storing a pressurized container of the present invention.

The pressurized containers useful in the invention include any containers in which a drug and a propellant can be stored. Slow leakage of propellant sometimes occurs in metered dose inhalers (MDIs) and the present invention is particularly useful in connection with MDIs that may have slow leaks.

The pressurized container is preferably an MDI or an MDI can. The term "metered dose inhaler" or "MDI" means a unit comprising a can, a crimped cap covering the mouth of the can, and a drug metering valve situated in the cap, while the term "MDI system" also includes a suitable channeling device. The term "MDI can" means the container without the cap and valve. The term "drug metering valve" or "MDI valve" refers to a valve and its associated mechanisms which delivers a predetermined amount of drug formulation from an MDI upon each activation. The channeling device may comprise, for example, an actuating device for the valve and a cylindrical or cone-like passage through which medicament may be delivered from the filled MDI can via the MDI valve to the nose or mouth of a patient, e.g. a mouthpiece actuator. The relation of the parts of a typical MDI is illustrated in U.S. Pat. No. 5,261,538 incorporated herein by reference. An exemplary MDI is disclosed in WO 96/26755, the entire contents of which is hereby incorporated by reference. Other exemplary pressurized containers for use in MDIs are disclosed in WO 96/32151, WO 96/32345, WO 96/32150 and WO 96/32099.

The pressurized container 34 is preferably a vial made from aluminum. However, other materials are not beyond the scope of the present invention. Other materials for the pressurized container 34 include, but are not limited to, ferrous alloys, non-ferrous alloys, such as stainless steel, ceramic materials, polymers, composite materials, and mixtures thereof. Suitable containers which contain a polymeric coating on the inside thereof are disclosed in WO 96/32151.

Most often the MDI can and cap are made of aluminum or an alloy of aluminum, although other metals not affected by the drug formulation, such as stainless steel, an alloy of copper or tin plate, may be used. An MDI can may also be fabricated from glass or plastic. Preferably, however, the MDI cans employed in the present invention are made of aluminum or an alloy thereof. Advantageously, strengthened aluminum or aluminum alloy MDI cans may be employed. Such strengthened MDI cans are capable of withstanding particularly stressful coating and curing conditions, e.g., particularly high temperatures, which may be required for certain fluorocarbon polymers. Strengthened MDI cans which have a reduced tendency to malform under high temperatures include MDI cans comprising side walls and a base of increased thickness and MDI cans comprising a substantially ellipsoidal base (which increases the angle between the side walls and the base of the can), rather than the hemispherical base of standard MDI cans. MDI cans having an ellipsoidal base offer the further advantage of facilitating the coating process.

The MDI cans include MDI cans supplied by Presspart of Cary, N.C., USA or the United Kingdom, or by Neotechnic of the United Kingdom. The MDI cans typically have a neck diameter of 20 millimeters, although any suitable neck diameter may be used and can vary in height from 30 millimeters to 60 millimeters.

The drug metering valve consists of parts usually made of stainless steel, a pharmacologically inert and propellant resistant polymer, such as acetal (polyoxymethylene), polyamide (e.g., Nylon®), polycarbonate, polyester, fluorocarbon polymer (e.g., Teflon®) or a combination of these materials. Additionally, seals and "O" rings of various materials (e.g., nitrile rubbers, polyurethane, acetyl resin, fluorocarbon polymers), or other elastomeric materials are employed in and around the valve.

The preferred MDI valves have typical metering chamber volumes of 25 to 63 microlitres. The valves preferably have a ferrule skirt to suit a 20 mm neck diameter can. Typical suppliers of MDI valves include Valois Pharm, France; Bespak of Europe or the United Kingdom; or Neotechnic, United Kingdom.

Drugs

Preferred drugs (also referred to as "medicaments") and drug combinations are disclosed in WO 96/32151, WO 96/32345, WO 96/32150 and WO 96/32099, the entire contents of which are hereby incorporated by reference. These drugs include, for example, fluticasone propionate or a physiologically acceptable solvate thereof, beclomethasone dipropionate or a physiologically acceptable solvate thereof, salmeterol or a physiologically acceptable salt thereof and albuterol or a physiologically acceptable salt thereof. Medicaments may be selected from, for example, analgesics, e.g. codeine, dihydromorphine, ergotamine, fentanyl or morphine, anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; anti-inflammatories, e.g. beclomethasone (e.g. the dipropionate), flunisolide, budesonide, tipredane or triamcinolone acetonide; antitussives, e.g. noscapine; bronchodilators, e.g. salbutamol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, orciprenaline, or (−)4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone;

xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimize the solubility of the medicament in the propellant.

Additionally, any suitable combination of drugs can be used in the present invention. For example, Seretide (fluticasone and Serevent) can be used in the present invention.

Propellants

"Propellants" used herein mean pharmacologically inert liquids with boiling points from about room temperature (25° C.) to about −25° C. which singly or in combination exert a high vapor pressure at room temperature, including CFCs such as Freon and hydrofluorocarbons. Upon activation of the MDI system, the high vapor pressure of the propellant in the MDI forces a metered amount of drug formulation out through the metering valve then the propellant very rapidly vaporizes dispersing the drug particles. The propellants used in the present invention are low boiling fluorocarbons; in particular, hydrofluorocarbons or hydrofluoroalkanes such as HFA-134a and HFA-227. The invention is particularly useful with propellants (including propellant mixtures) which are more hygroscopic than P11, P114 and/or P12 such as HFA-134a and HFA-227.

Additional Components of the Drug Formulation

The MDIs taught herein are particularly useful for containing and dispensing inhaled drug formulations with hydrofluoroalkane propellants such as 134a with little, or essentially no, excipient and which tend to deposit or cling to the interior walls and parts of the MDI system. In certain cases, it is advantageous to dispense an inhalation drug with essentially no excipient, e.g., where the patient may be allergic to an excipient or the drug reacts with an excipient.

Drug formulations for use in the invention may be free or substantially free of formulation excipients, e.g., surfactants and cosolvents, etc. Such drug formulations are advantageous since they may be substantially taste and odor free, less irritant and less toxic than excipient-containing formulations. Thus, a preferred drug formulation consists essentially of a drug, or a physiologically acceptable salt or solvate thereof, optionally in combination with one or more other pharmacologically active agent, and a fluorocarbon propellant.

Further drug formulations for use in the invention may be free or substantially free of surfactant. Thus, a further preferred drug formulation comprises or consists essentially of a drug (or a physiologically acceptable salt or solvate thereof), optionally in combination with one or more other pharmacologically active agents, a fluorocarbon propellant and 0.01 to 5% w/w based on the propellant of a polar cosolvent, which formulation is substantially free of surfactant. Preferred propellants are 1,1,1,2-tetrafluoroethane, 1,1,1,2,3,3,3-heptafluoro-n-propane or mixtures thereof, and especially 1,1,1,2-tetrafluoroethane or 1,1,1,2,3,3,3-heptafluoro-n-propane. However, the drug formulation may contain any additional excipients which are necessary or desirable to prepare a suitable drug formulation.

The term "excipients" as used herein means chemical agents having little or no pharmacological activity (for the quantities used) but which enhance the drug formulation or the performance of the MDI system. For example, excipients include but are not limited to surfactants, preservatives, flavorings, antioxidants, antiaggregating agents, and cosolvents, e.g., ethanol and diethyl ether.

Suitable surfactants are generally known in the art, for example, those surfactants disclosed in European Patent Application No. 0327777. The amount of surfactant employed is desirably in the range of 0.0001% to 50% w/w ratio relative to the drug, in particular 0.05 to 5% w/w ratio.

A polar cosolvent such as $C_{2-6}$ aliphatic alcohols and polyols, e.g., glycerol, ethanol, isopropanol and propylene glycol, preferably ethanol, may be included in the drug formulation in the desired amount, either as the only excipient or in addition to other excipients, such as surfactants. Suitably, the drug formulation may contain 0.01 to 5% w/w based on the propellant of a polar cosolvent, e.g., ethanol, preferably 0.1 to 5% w/w, e.g., about 0.1 to 1% w/w.

Flexible Packaging Materials

The flexible packaging material can be any material which is impervious to or substantially impervious to moisture. The packaging material is preferably permeable to propellants such as HFA-134a and/or HFA-227 whereby if the propellant slowly leaks from the pressurized container, the propellant will slowly pass, by diffusion or otherwise, through the packaging material.

For ease of manufacturing, and in order to provide the necessary properties to the packaging material, the flexible packaging material preferably comprises a non-thermoplastic substrate (such as a metal foil) and a heat sealable layer disposed thereon, and an additional protective layer, such as a polymer film of polyester. The heat sealable layer is usually disposed on the inner surface of the assembled package. The additional protective layer is usually disposed on the surface opposite the heat sealable layer. An example of a particularly useful foil laminate is a polyester film adhesively laminated to aluminum foil adhesively laminated to Ionomer (SURLYN™) film, for example, $12\mu$ polyester/$9\mu$ aluminum/$50\mu$ ionomer film supplied by Lawson Mardon Singen (LMS).

The substrate is preferably formed from aluminum foil. However, other metals for the substrate include, but are not limited to, tin, iron, zinc, or magnesium formed on a sheet by vacuum deposition or sputtering and a carboxyl group-containing polyolefin layer formed on the metal layer by lamination.

The heat sealable layer can be formed from any thermoplastic or thermosetting material such as an ionomer resin, polyolefin, or cydoolefin copolymer, Ionomer resins typically include ionically cross-linked ethylene-methacrylic acid and ethylene acrylic acid copolymers. Properties which distinguish these ionomers resins from other polyolefin heat-sealed polymers are high clarity, high impact resistance, low haze in lamination, tear resistance, abrasion resistance, solid state toughness, and moisture imperviousness. In the preferred embodiment, the heat sealable layer is made out of SURLYN™ (an ionomer resin) or a form of polyethylene to provide sufficient heat sealing properties.

The outer protective layer, if present, can be formed of any material as long as the final laminate has the requisite properties.

Preferably, the protective layer (e.g., polyester) is adhesively laminated to the substrate (e.g., aluminum) and the substrate layer in turn is adhesively laminated to the heat sealable layer (e.g., the ionomer film or SURLYN™ (an ionomer resin)).

Preferred exemplary thicknesses of the three layers include a protective layer 1 to 40, preferably 4 to 30, more preferably 10 to 23 microns, and most preferably 12 microns; a substrate layer of 1 to 100, preferably 3 to 70, more preferably 5 to 50 microns, more preferably 6 to 20 microns and most preferably 9 microns. For the heat sealable layer, preferred exemplary thicknesses include thicknesses of 1 to 100, preferably 5 to 70, more preferably 10 to 60, more preferably 20 to 55 microns, and most preferably 50 microns.

Adhesives may be used to join the respective layers of materials together. The adhesive layers are typically substantially smaller in thickness relative to the thickness of the substrate, heat sealable and/or protective layers which they bond.

The number, size, and shape of the layers are not limited to those layers shown in the drawings. Any number of layers with relative areas of any size and predetermined thicknesses may be used so long as the flexible package forms an enclosed volume which substantially prevents ingression of water vapor and particulate matter into the enclosed volume while permitting egression out of the enclosed volume of any propellant leaving the pressurized container. The size, shape, and number of layers of the package is typically a function of the size and contents of the pressurized container which includes a drug and a propellant.

The package is believed to operate similarly to a virtual one-way valve due to the composition of the layers and due to the transmission rate of water vapor molecules into the enclosed volume relative to the transmission rate of gas molecules of a propellant, such as a hydrofluoroalkane, out of the enclosed volume. The package permits the propellant in the pressurized container to diffuse out of the enclosed volume while substantially preventing water vapor and other particulate matter from entering the enclosed volume. Excess or leakage of the propellant is permitted to egress from the package. The virtual one-way valve function of the package prevents or minimizes the chance of any sudden ruptures or prevents or minimizes unexpected expulsion of the propellant during opening of the package.

Moisture Absorbing Materials

The moisture absorbing material is preferably a silica gel desiccant sachet. However, other vapor or moisture absorbing mechanisms are not beyond the scope of the present invention. Other vapor or moisture absorbing materials include desiccants made from inorganic materials such a zeolites and aluminas. Such inorganic materials of vapor or moisture absorbing materials have high water absorption capacities and favorable water absorption isotherm shapes. The water absorption capacity of such materials typically varies from 20 to 50 weight percent.

In the preferred embodiment, the absorbing material is a MINIPAX® supplied by Multisorb Technologies in the United States and Silgelac in Europe (silica gel packaged inside TYVEK®, which is a nylon mesh bonded with a microporous polyurethane). Other exemplary moisture absorbing materials include, but are not limited to, alumina, bauxite, anhydrous, calcium sulfate, water-absorbing clay, activated bentonite clay, a molecular sieve, or other like materials which optionally include a moisture sensitive color indicator such as cobalt chloride to indicate when the desiccant is no longer operable. While in the preferred embodiment of the present invention, the package is designed to substantially prevent ingression of water vapor and particulate matter into the enclosed volume, the moisture absorbing material is placed within the enclosed volume in order to absorb any residual moisture present in the atmosphere or on the external surface of the pressurized container or mouthpiece or a combination thereof, prior to sealing the package.

The desiccant should be present in an amount sufficient to absorb any residual moisture inside the package or which might escape from inside the pressurized container. When silica gel is used, 1 g to 10 g of silica gel is sufficient for a typical MDI. Moreover, the desiccant should be present in an amount sufficient to absorb any moisture that possibly ingresses from the external environment.

It is also possible to place the desiccant inside the container, either loose in the canister or as part of an assembly attached to the canister.

The Container Storage System

Referring in detail to the drawings and with particular reference to FIG. 1, a container storage system (or packaged product) 20 is shown. The container storage system 20 includes a package or wrapping 22 that employs multi-layers of material 24, 26, 28. (See FIG. 4.) The package 22 further includes fin seams 30, 32 which are disposed along two parallel side edges of the package and along a single longitudinal edge of the package 22.

The number and type of fin seams 30, 32 are not limited to the types shown in the drawings. The package 22 can include additional seams or significantly fewer seams such as a continuous single seam. The orientation of the seams 30, 32 is not limited to the orientation shown in the drawings. The orientation of the seams 30, 32 is typically a function of the sealing device and such seams may be oriented in a manner which substantially increases manufacturing efficiency. During manufacture, the longitudinal seam 30 may be formed first by heat sealing and the two end seams 32 may then be formed by heat sealing to close the package. Other types of seams include, but are not limited to, gusset type seams which include excess material which provides expansibility, stitched type seams, or mechanically crimped seams, and other like structures.

Figure 3:
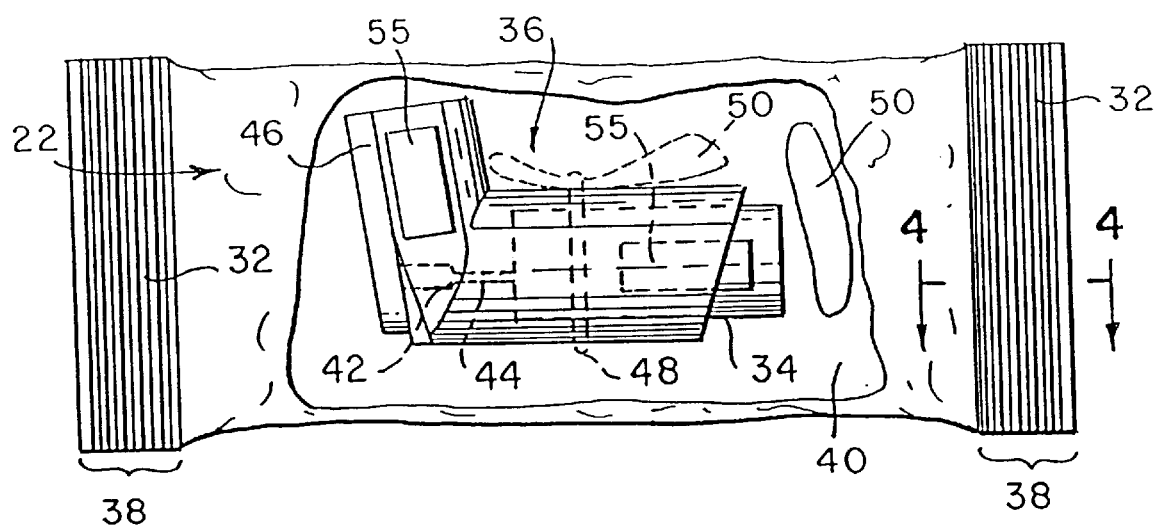
FIG. 3 is a cutaway bottom view of the package for storing a pressurized container of the present invention.

The container storage system includes a pressurized container 34 which is preferably part of an MDI 36 (see FIG. 3). While the preferred pressurized container 34 is part of an MDI 36, other devices which include pressurized containers 34 are not beyond the scope of the present invention.

The fin seams 30 and 32 are formed by a conventional heat sealing device which mechanically crimps sides of the package 22 together while simultaneously providing heat to the sides 30, 32. The heat sealing device typically has electrical heater elements shaped to produce the pattern of the fin seams 30, 32 where the fin seams include multiple ridges 38. The sealing mechanism of the container storage system 20 of the present invention is not limited to heat sealing devices. Other sealing devices include, but are not limited to, glue sealing machines, sonic welding machines, electron beam radiation machines, and other like sealing devices.

Figure 2:
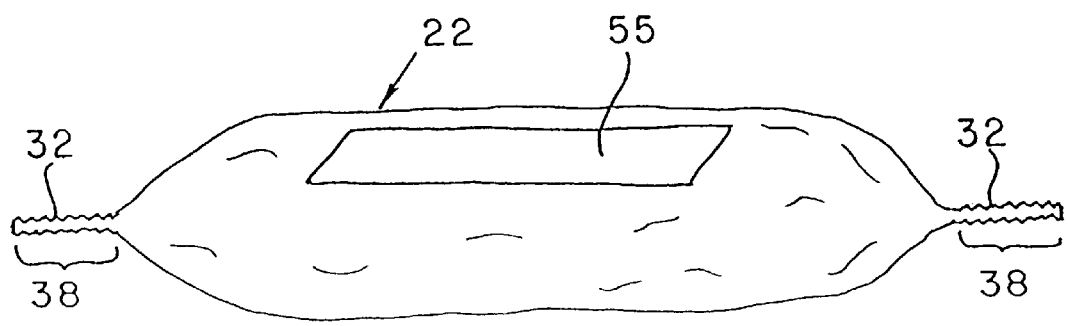
FIG. 2 is a side view of the package for storing a pressurized container of the present invention.

As seen in FIGS. 1 and 2, the package 22 preferably has a substantially rectangular configuration with a substantially elliptical cross section, however, other shapes of the package 22 are not beyond the scope of the present invention. Other shapes include, but are not limited to circular, square, triangular, trapezoidal, pentagonal, hexagonal, octagonal, and other like shapes. The shape of the package 22 is preferably a function of the shape of the enclosed pressurized container 34 as well as the amount and type of storage space since the package 22 is made from flexible materials as will be described in further detail below.

As seen in FIG. 3, the package 22 provides an enclosed volume 40 in which the pressurized container 34 is disposed therein. The size of the enclosed volume 40 can be adjusted according to the size of the pressurized container 34 and related parts thereto. Preferably, the enclosed volume 40 is of a size which permits relative ease of closing respective sides and layers 24, 26 and 28 without substantial stretching of the package 22. The enclosed volume 40 may be substantially evacuated prior to formation of the fin seams 30, 32 to substantially reduce any water vapor being present in the enclosed volume 40. The enclosed volume 40 may be evacuated to such a degree that the enclosed volume 40 is a vacuum region around the pressurized container 34. While the enclosed volume 40, may remain constant, its relative shape may change according to shifting of the pressurized container 34 disposed within the enclosed volume 40.

The amorphous shape of the enclosed volume 40 is attributed to the flexible materials which make up the layers 24, 26, 28 of the package 22 which will be discussed in further detail below. The enclosed volume can be varied in size such that it substantially conforms to the shape of the pressurized container 34 and any related parts thereto or such that the enclosed volume 40 is larger than the pressurized container 34, as shown in FIG. 3. When the enclosed volume is of a size which is substantially equivalent with the surface area of the pressurized container 34 and related parts, the layers 24, 26, and 28 of material substantially conform to the shape of the pressurized canister 34 and related parts. The package is preferably placed in a separate, more rigid container, such as a paperboard or cardboard box 74 (See FIG. 6) typically used in the pharmaceutical industry. The package may expand during storage due to slow leakage of the propellant from the pressurized container. In this situation, the shape of the package may conform to some extent to the internal shape of the rigid container if the volume of the rigid container is just slightly larger than the expanded volume of the flexible package.

In one exemplary embodiment, FIG. 3 shows the pressurized container 34 to be connected to a nozzle 42 by a valve stem 44. The pressurized container 34 is preferably an aluminum metal vial having a metering valve 60 (See FIG. 5) disposed therein which is connected to the valve stem 44. The pressurized container 34 is not limited to the nozzle 42 and valve stem 44 shown and the metering valve 60. While the pressurized container 34 preferably includes a metering valve, other valve systems are not beyond the scope of the present invention. Other valve systems include, but are not limited to, wedge gate valve systems, double-disc gate valve systems, globe and angle valve systems, swing check valve systems, end cock valve systems, and other like valve systems. Since the pressurized container 34 is preferably part of an MDI, the valve design is typically a function of providing a predetermined dosage or amount of the drug contained within the pressurized container 34 to a user.

The nozzle 42 is typically fixably secured to the mouthpiece 46. However, other embodiments where the nozzle 42 is separate or detached from the mouthpiece 46 is not beyond the scope of the present invention. The pressurized canister 34, the nozzle 42, and the mouthpiece 46 together comprise an MDI 36.

As seen in FIG. 3, nozzle 42 is in fluid communication with the mouthpiece 46 so that upon movement of the pressurized container relative to the mouthpiece 46 in a direction where the pressurized container 34 moves towards the nozzle 42 fixed to one side of the mouthpiece 46, a metered dosage or predetermined amount of the drug and propellant contained within the pressurized container 34 is released. Such a combination of the fixed nozzle 42, mouthpiece 46, valve stem 44, and pressurized container 34 form an MDI 36 as outlined above.

The MDI 36 can be packaged by the flexible packaging material 22 in either an assembled state (valve stem 44 fixed to nozzle 42) or a disassembled state (valve stem 44 detached from nozzle 42). In a preferred embodiment, the moisture absorbing material 50 lays adjacent to the mouthpiece 46 in a loose or free flowing manner. Alternatively, the moisture absorbing material can be secured to the inside of the flexible package. In another alternative embodiment, the moisture absorbing material may be disposed within the container 34 or attached to a bracket structure such as a ring which is fastened to the container 34.

In one possible embodiment, the moisture absorbing material may be attached to the external surface of the mouthpiece 46 by a fastening device such as a rubber band 48. The fastening device 48 is preferably a removable elastic mechanism such as a rubber band. However, other fastening devices are not beyond the scope of the present invention. Other fastening devices include, but are not limited to, adhesives, adhesive tapes, shrink-wrap plastic, fasteners such as screws, nails, or rivets, compartments which are part of the mouthpiece housing 46, and other like attachment devices.

The mouthpiece 46 substantially encloses pressurized container 34. The mouthpiece 46 is preferably simple in structure so that manufacturing efficiency and economy is substantially increased. However, other mouthpieces 46 are not beyond the scope of the present invention. Other mouthpieces include, but are not limited to, relatively movable mouthpieces with multiple parts, mouthpieces which also include a protective casing substantially surrounding the mouthpiece protecting the mouthpiece 46 from damage due to shock, and other like mouthpiece structures.

The pressurized container 34 may be held in the mouthpiece 46 by ribs or projections (not shown) extending from walls of the mouthpiece so that the pressurized container 34 is in a press-fit engagement with the mouthpiece 46. The valve stem 44 also provides a secure connection to the nozzle 42 which is fixedly secured to the mouthpiece 46. Other types of supporting mechanisms which hold the pressurized container 34 within the mouthpiece 46 are not beyond the scope of the present invention. Other types of securing or supporting mechanisms include, but are not limited to, fasteners such a screws, nails, or rivets, adhesives, mouthpieces with a female or male locking/keying mechanism which engages with a predetermined shape of the pressurized container, or other like supporting structures.

In the preferred embodiment of the invention, the support mechanisms, such as ribs or projections (not shown) of the mouthpiece 46 are designed for manufacturing efficiency which in turn reduces cost of the overall manufacturing process of the mouthpiece 46. The mouthpiece 46 is preferably made of plastic, however other materials are not beyond the scope of the present invention. Other materials for the mouthpiece 46 include, but are not limited to, ferrous alloys, non-ferrous alloys, ceramic materials, and composite materials and any mixtures thereof. Similar to the mouthpiece, the valve stem 44 is preferably made of plastic, but other materials are not beyond the scope of the present invention. Other materials for the valve stem 44 include, but are not limited to, ferrous alloys, non-ferrous alloys, ceramic materials, composite materials, and any mixtures thereof.

The pressurized container 34 preferably includes a liquid stored within the pressurized container 34 at a predetermined pressure. The liquid preferably includes a drug dispersed or dissolved therein such as salmeterol or fluticasone propionate.

Figure 4:
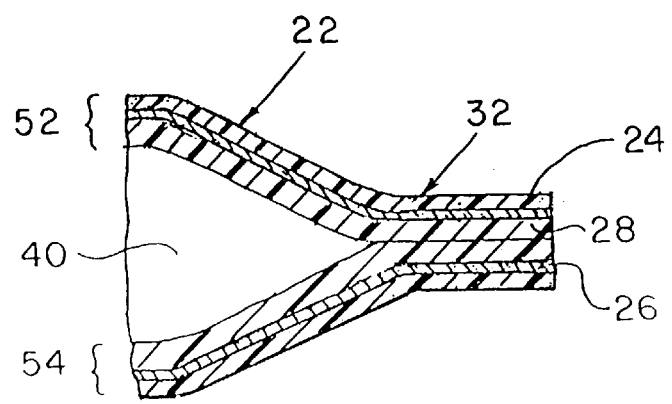
FIG. 4 is a cross-sectional view of the package for storing a pressurized container of the present invention.

In FIG. 4, a cross-sectional view of the package 22 is shown. Fin seams 32 include two peripheral edges 52, 54 of the flexible packaging material. The flexible packaging material comprises a first layer 24, a second layer 26, and a third, preferably heat sealable, layer 28 of material. The first layer 24 and third layer 28 are preferably made from polymers. The first layer 24 is preferably made out of polyester while the third layer 28 is preferably made out an ionomer resin. The second layer 26 is preferably made of a metal foil. In the preferred embodiment, the metal foil is made out of aluminum. In an alternative embodiment, the heat sealable layer is a polyethylene film.

As stated above, preferably, the protective layer (e.g., polyester) is adhesively laminated to the substrate (e.g., aluminum) and the substrate layer in turn is adhesively laminated to the heat sealable layer (e.g., the ionomer film or SURLYN™ (an ionomer resin) or a polyethylene film).

Preferred exemplary thicknesses of the three layers include a protective layer made of a polyester film having a thickness of 1 to 40, preferably 4 to 30, more preferably 10 to 23 microns, and most preferably 12 microns; a substrate layer made of aluminum having a thickness of 1 to 100, preferably 3 to 70, more preferably 5 to 50 microns, more preferably 6 to 20 microns, and most preferably 9 microns. For the heat sealable layer, an ionomer film is used having a preferred exemplary thicknesses of 1 to 100, preferably 5 to 70, more preferably 10–60, more preferably 25–5 microns, and most preferably 50 microns. In an alternative embodiment, a heat sealable layer of polyethylene film is used having a preferred thicknesses of 1 to 100, preferably 5 to 70, more preferably 10–60, more preferably 20–50 microns, and most preferably 50 microns.

Preferred exemplary embodiments include a polyester film as the protective layer having a thickness ranging from 12 to 23 microns. The polyester film is laminated to an aluminum foil as the substrate layer having a thickness ranging from 6 to 20 microns. The aluminum foil is laminated to a sealing film such as either an inomer film having a thickness ranging from 25 to 50 microns or a polyethylene film having a thickness ranging from 20 to 50 microns.

Alternative preferred embodiments include aluminum metalized polyester film laminated to a heat sealable layer as outlined above. Another embodiment includes a silicon oxide coplated polyester film laminated to a heat sealable layer as outlined above. Yet, in another embodiment, a polyester film as a protective layer having a thickness ranging from 12 to 30 microns is laminated to an aluminum foil substrate layer having a thickness ranging from 6 to 20 microns, the aluminum foil being laminated to a polyester film of 12 to 30 microns which is laminated to a heat sealable layer as outlined above. In another embodiment, a polypropylene film as a protective layer having a thickness ranging from 15 to 30 microns is laminated to an aluminum foil substrate layer having a thickness ranging from 6 to 20 microns, and the aluminum foil is laminated to a heat sealable layer as outlined above. The laminates of the present invention can be adhesively laminated or extrusion laminated.

The general structure for the preferred embodiment of the present invention is as follows: OUTSIDE ENVIRONMENT, POLYESTER FILM 24, ALUMINUM FOIL 26, IONOMER FILM 28, ENCLOSED VOLUME 40, IONOMER FILM 28, ALUMINUM FOIL 26, POLYESTER FILM 24, OUTSIDE ENVIRONMENT. (See FIG. 4.)

The lines in the drawings which show the boundaries between respective layers 24, 26, and 28 may be considered as adhesive layers if adhesives are used to join the respective layers. In other words, for example, the line separating protective layer 24 from the metal foil layer 26 may be interpreted as an adhesive, if an adhesive is used to join these layers 24, 26.

Figure 5:
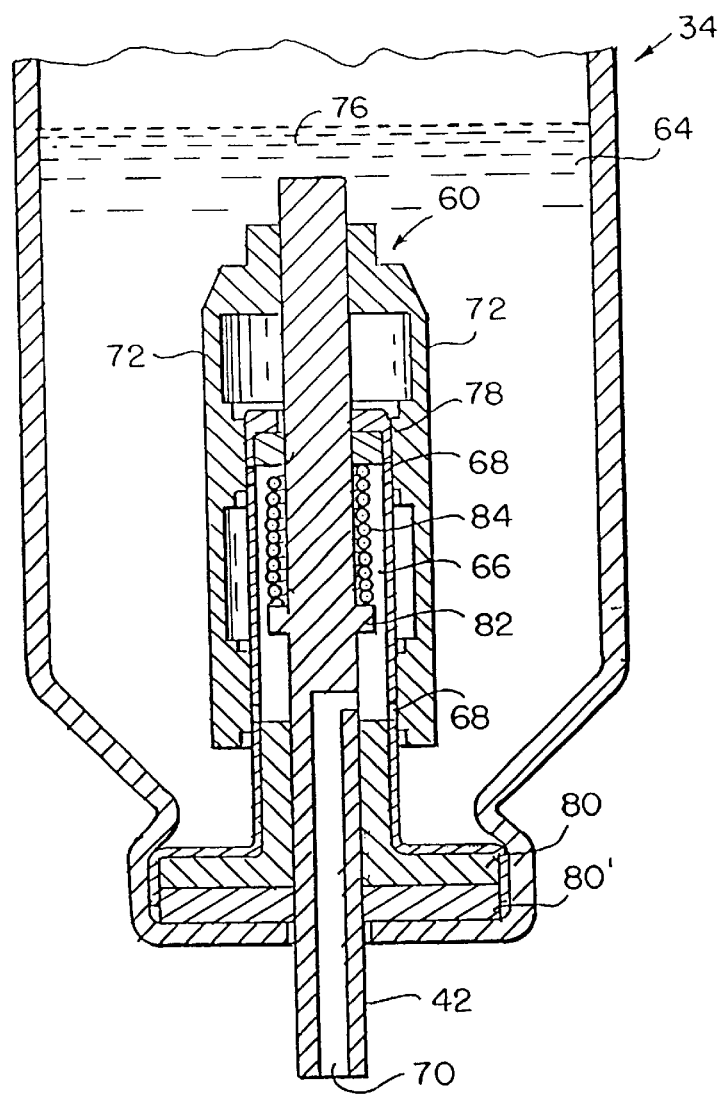
FIG. 5 is a cross sectional view of a metering valve which could be used in the present invention.

FIG. 5 shows an exemplary fluid dispensing apparatus 36 containing a metered aerosol dispensing valve 60 which dispenses metered amounts of fluid material 76 from a reservoir 64. The fluid dispensing apparatus (or metered dose inhaler) may also be packaged as an article of manufacture (shown in FIGS. 2, 3, or 6) comprising an aerosol dispensing valve 60 of the present invention, an integral or additional dispensing apparatus, and a safe and therapeutically effective amount of a medicament in a pharmaceutically acceptable carrier, particularly a propellant. The medicament and carrier can also contain other medications and various excipients.

The packaging material of the article of manufacture may also have labeling 55 and information relating to the composition contained therein and/or printed thereon, such as by an adhesive label secured to the exterior of the flexible package. Additionally or alternatively, the article of manufacture of the present invention may have a brochure, report, notice, pamphlet, or leaflet 65 containing product information. This form of product information is sometimes, in the pharmaceutical industry, called the "package insert." A package insert 65 may be attached to or included with the article of manufacture. The package insert will usually be provided inside the box 74 but outside the flexible package. The package insert 65 and any article of manufacture labeling provides information relating to the composition and use of the product. This information and labeling provides various forms of information utilized by health care professionals and patients that describes the composition, the dosage, the use, and various other parameters of the medicament required by regulatory agencies, such as the United States Food and Drug Administration.

Figure 6:
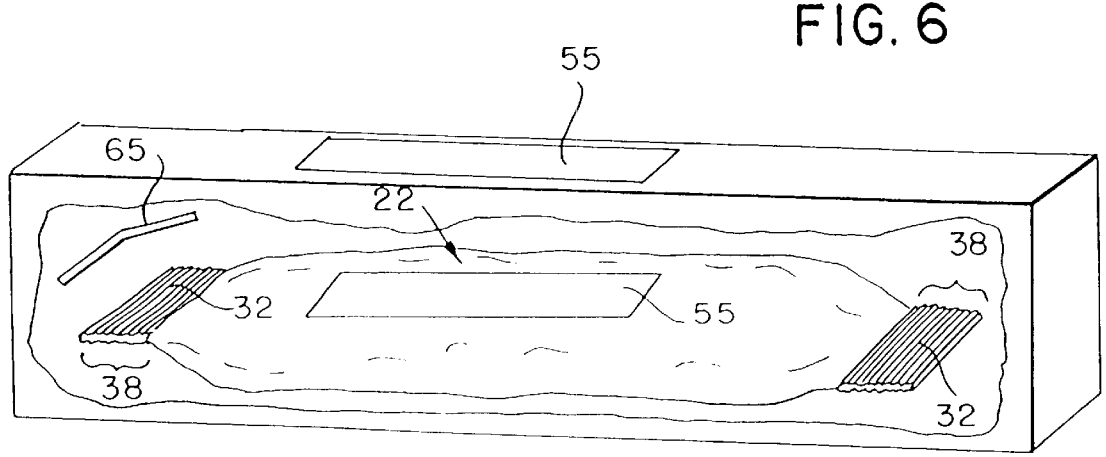
FIG. 6 is a side view of the second container with a product label which is placed over the wrapping means of the present invention.

FIGS. 5 and 6 show an article of manufacture including packaging material 22, a fluid dispensing apparatus or MDI 34 for dispensing metered amounts of fluid material 76 from a reservoir 64. In one exemplary embodiment, the fluid dispensing apparatus 34 can include a container 34 defining a reservoir 64, and a dispensing valve 60. The dispensing valve 60 can include a metering chamber body 62, defining a metering chamber 66 and having one or more metering chamber ports 68; and a stem 42 allowing for slideable movement within the metering chamber body 62. The stem 42 has a dispensing passage 70 and is connected to a sealing segment 72 allowing for slideable movement over the one or more metering chamber ports 68. The present invention is not limited to the fluid dispensing apparatus shown in FIG. 5 and can include other types of fluid dispensing devices.

The stem 42 and sealing segment 72 can be moveable such that in a first position the metering chamber 66 is fluidically isolated from the dispensing passage 70, and the metering chamber 66 is in fluidic communication with the reservoir 64 through the one or more metering chamber ports 68 and the dispensing passage 70. In a second position (as shown in FIG. 5), the metering chamber 66 is in fluidic communication with the dispensing passage 70; and the metering chamber 66 is fluidically isolated from the reservoir 64 by the sealing segment 72 occluding the one or more metering chamber ports 68 and the stem occluding the dispensing passage 70. Also shown in FIG. 5, is fluid material 76 containing a safe and effective medicament and a pharmaceutically acceptable carrier or diluent or propellant.

The dispensing valve 60 can further include an upper sealing sleeve 78 and lower sealing sleeves 80 and 80'. Stem 42 is positioned for slideable movement within metering chamber 7 through the lower and upper aperture containing lower sealing sleeves 80 and 80' and the upper sealing sleeve 78.

Flange 82 and spring 84 define the limits of travel for stem 42. Within these limits of travel, the stem 42 occupies an infinite number of positions which include the above mentioned first and second positions. In FIG. 5, stem 42 is biased toward the upper sealing sleeve 78 in the second position by physical force exerted by a user.

In FIG. 6, a box 74 encloses the container storage system 20. On the exterior of the box 74, a label 55 is disposed which provides information relating to the composition contained within the MDI. The label 55 may be located on any side of the box 74, that is most beneficial to the user. Further, as mentioned above, a package insert 65 may be disposed within the box 74 and outside the container storage system 20.

The present invention also provides a method of storing a container 34 including the steps of providing a flexible package 22 where the package 22 includes layers 24, 26, and 28 of material which are collectively impermeable to water vapor and permeable to vaporized propellant.

The method includes the step of filling the container 34 with the liquid propellant at a predetermined pressure and wrapping the container 34 with the flexible package 22 to form an enclosed volume 40 in which the first container 40 is disposed therein.

The method further includes sealing the flexible package 22 which in turn closes the enclosed volume 40, so that the flexible package 22 substantially prevents ingression of water vapor and particulate matter into said enclosed volume 40 while permitting egression of said vaporized propellant, whereby shelf life and performance of the drug and the propellant are increased. The packaged product can be stored for prolonged periods of time such as 1 month or more, 3 months or more or 6 months or more at temperatures such as 25, 30 or 40° C. and at relative humidities of 60 or 75% while maintaining acceptable product properties.

The invention further includes method steps drawn to providing a material 50 for absorbing moisture in the enclosed volume 40 and disposed adjacent to the container 34.

Figure 7:
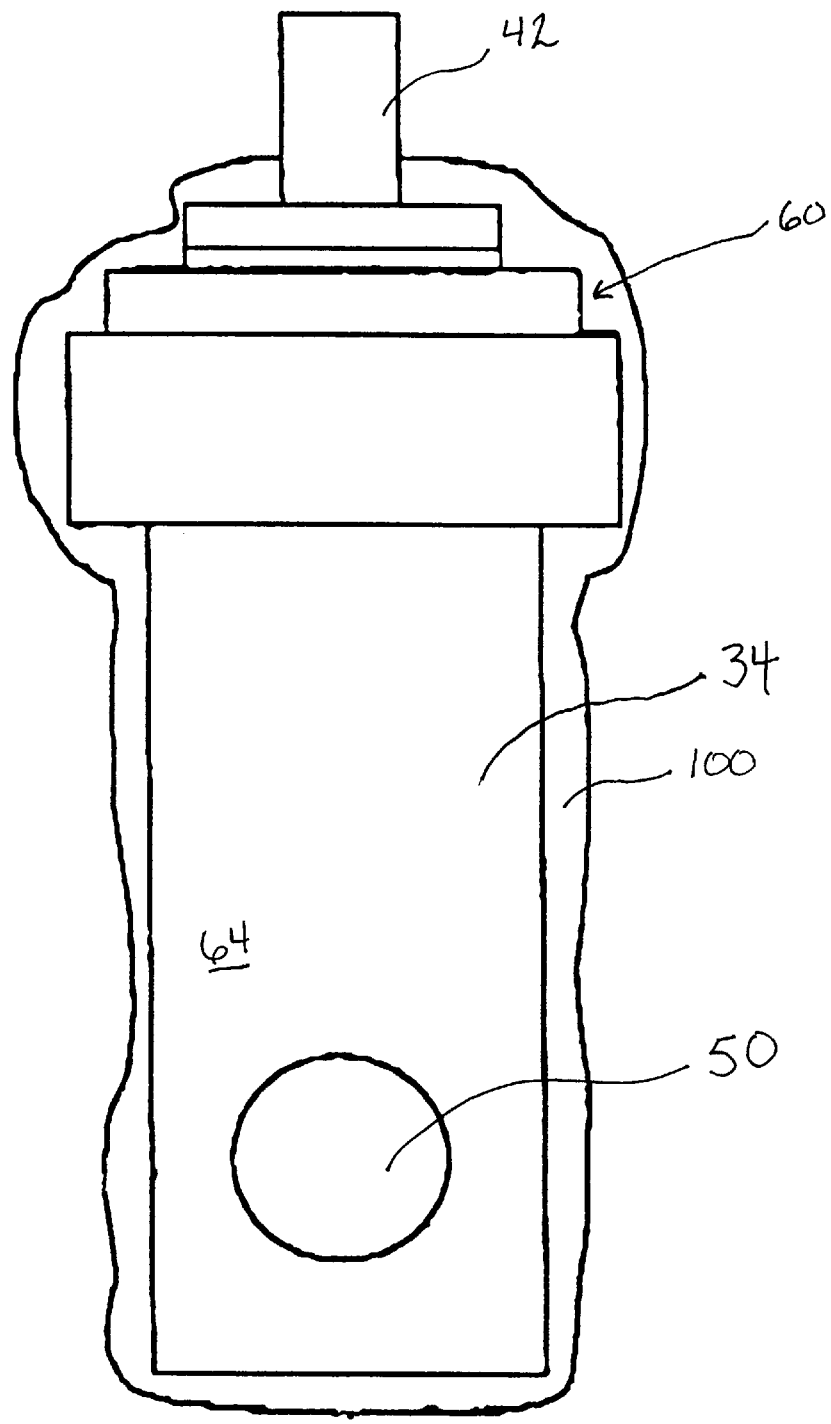
FIG. 7 is a cross sectional view of the moisture-absorbing, heat shrink wrapped MDI of the present invention.

Shown in FIG. 7 is a cross sectional view of the moisture-absorbing, heat shrink wrapped MDI of the present invention. The fluid dispensing device includes a pressurized container 34 having a valve assembly 60 and a stem 42. In addition to the drug and HFA propellant, the reservoir 64 of the container 34 contains a desiccant 50 for absorbing any moisture within the MDI. The internal desiccant 50 is optional, particularly where a moisture-absorbing shrink wrap (or sleeve) 100 is employed and heat shrinked onto the MDI. Preferably, the shrink wrap 100 includes a polymeric or adhesive layer impregnated with a desiccant. The shrink wrap 100 also preferably includes an oriented polymer layer that shrinks predominately more in one direction so as to provide more enhanced sealing at the interface 102 between the stem and the valve assembly 60 and/or the interface 104 between the valve assembly 60 and the cannister 34. The heat shrink wrap 100 does not cover the stem 42 in order to eliminate the need to remove the wrap 100 before the MDI is put into use. Thus, the MDI having the moisture absorbing heat shrink wrap shown in FIG. 7 (with or preferably without the internal desiccant 50) advantageously reduces moisture ingress into the MDI.

EXAMPLES AND COMPARATIVE TESTS/ ANALYSIS

In order to evaluate the effectiveness of the method and package for storing a pressurized canister of the present invention, shelf-life tests were carried out upon packages 22 which contained MDIs such as salmeterol/HFA-134a inhalers, Albuterol/HFA-134a, and Fluticasone Propionate/HFA-134a inhalers. A first shelf-life test of Albuterol/HFA-134a inhalers showed that by placing an MDI into the package 22 containing silica gel desiccant or an absorbing mechanism 50, it was possible to substantially reduce the amount of moisture ingression (measured in Parts Per Million or PPM) into the inhaler after three months of storage at 40° C. and at 85% relative humidity. See Table 1.

TABLE 1

| Sample | Initial | 1 month @ 40° C./ 85% RH | 3 months @ 40° C./ 85% RH |
| --- | --- | --- | --- |
| Control (non overwrapped inhaler) | 35 ppm | 330 ppm | 446 ppm |
| Inhaler sealed in foil overwrap with 10 g silica gel desiccant | 35 ppm | 106 ppm | 178 ppm |
| Inhaler stored in Zantac Efferdose tube | 35 ppm | 158 ppm | 198 ppm |

Also included in Table 1 is data for MDIs which are stored in the prior art type tube containers. The prior art type tubes included a ZANTAC™ EFFERDOSE™ tube. This type of tube is a plastic tube which contains silica gel desiccant. The silica gel is disposed in a resealable lid that closes the tube. This tube construction is similar to that used for a Schering product, VANCERIL™ double strength.

A second test was performed and the results indicate that the reduction of moisture content within the package 22 (which in the second test included the desiccant 50) can improve overall product performance of the liquid contained within the pressurized container 34, where the liquid includes an asthma treating drug and a propellant. In the second test, the experiment was performed where aged non-overwrapped salmeterol/HFA-134a inhalers were compared to MDIs provided in the package 22. The experiment included non-overwrapped inhalers which were stored for three months at either 30° C./60% relative humidity or 40° C./75% relative humidity. The non-overwrapped inhalers were then placed in a desiccator containing phosphorous pentoxide. The non-overwrapped inhalers were then tested for moisture content and fine particulate mass (FPM—the moisture sensitive product performance test over the period of inhaler storage). The results of this test are presented in Table 2.

TABLE 2

| | 30° C./60% RH | | 40° C./75% | |
| --- | --- | --- | --- | --- |
| Time | Moisture content, PPM | FPM, Mcg | Moisture content, PPM | FPM, Mcg |
| Initial | 92 | 10.3 | 92 | 10.3 |
| 1 month non overwrapped | Not tested | Not tested | 412 | 8.2 |
| 3 month non overwrapped | 463 | 7.9 | 616 | 6.2 |
| 6 weeks storage | 233 | 8.9 | 298 | 7.4 |
| 13 weeks storage | 151 | 9.4 | 230 | 8.0 |

The data in Table 2 shows that loss and product performance (loss in FPM, for salmeterol) is directly related to change in moisture content. The results indicated that product performance of MDIs is reversible, although not 100% reversible. Therefore, if moisture causes loss in product performance, it is possible to retrieve and improve the product performance by removing moisture from the MDI during storage. Such is the result with the package 22 of the present invention. Thus, the data shows how product performance is improved by controlling the moisture content within the MDI with the present invention.

A third comparative stability test at various elevated storage conditions was performed on a batch of Salmeterol/HFA134a Inhalers that were overwrapped shortly after manufacture and compared against a control of non-overwrapped inhalers from the same batch. The FPM and moisture determinations are summarized in Table 3 and 4. Table 3 shows the FPM over six months for the control group non-overwrapped MDIs compared to overwrapped MDIs (contained within the package 22 of the present invention). Table 4 shows the inhaler moisture content in Parts Per Million (or PPM) over six months for the control group of non-overwrapped meter dose inhalers compared to MDIs provided in the package 22 of the present invention.

The data in Table 3 shows that the fine particulate mass (FPM), measured in micrograms (µg), of the MDIs provided in the package 22 of the present invention decreases at a substantially slower rate than that of the control group of non-overwrapped meter dose inhalers. The data in Table 4 shows that the moisture content in part per million (ppm) over six months for the MDI provided in the package 22 of the present invention is less than the moisture content present adjacent to or within the MDIs which are not provided with any overwrap.

TABLE 3

Fine Particulate Mass (in µg)

| Time point (months) | 40° C./75% RH | | 25° C./60% RH | | 25° C./75% RH | |
|---|---|---|---|---|---|---|
| | Control | wrapped | Control | Wrapped | Control | wrapped |
| 0 | 9.4 | 9.4 | 9.4 | 9.4 | 9.4 | 9.4 |
| 1 | 7.8 | 8.6 | 8.4 | 8.6 | 8.4 | 8.7 |
| 3 | 6.0 | 7.4 | 8.3 | 8.5 | 8.0 | 8.3 |
| 6 | 6.2 | 7.7 | 7.5 | 7.8 | 7.2 | 7.8 |

TABLE 4

Moisture Content (in ppm)

| Time point (months) | 40° C./75% RH | | 25° C./60% RH | | 25° C./75% RH | |
|---|---|---|---|---|---|---|
| | Control | wrapped | Control | Wrapped | Control | wrapped |
| 0 | 81 | 81 | 81 | 81 | 81 | 81 |
| 1 | 360 | 63 | 194 | 71 | 217 | 93 |
| 3 | 540 | 29 | 405 | 45 | 434 | 64 |
| 6 | 526 | 93 | 446 | 76 | 485 | 47 |

A fourth comparative test was performed on a control group of non-overwrapped MDIs containing fluticasone propionate/HFA-134a compared to MDIs of the same drug and propellant provided in the package 22 of the present invention. The MDIs of the present invention were manufactured and provided in the package 22 of the present invention shortly after the time of manufacture and placed on stability at various elevated storage conditions along side the control group of unwrapped inhalers from the same batch.

Table 5 of the fourth test summarizes the variation in the content uniformity at the six-month time period in addition to the moisture of the control group and the MDIs provided in the package 22 of the present invention. Table 5 shows the variation in content uniformity in percentage of the relative standard deviation (RSD) based on the values for a dose ex actuator obtained from ten cans at the end of use (final nominal use). This variation test was obtained over six months for the control group of non-overwrapped MDIs compared with MDIs provided in the package 22 of the present invention.

Table 6 shows the inhaler moisture content in parts per million or PPM over six months for the control group of non-overwrapped MDIs of the fluticasone propionate/HFA-134a type compared to MDIs of the same drug and propellant provided in the package 22 of the present invention. Table 5 demonstrates that the MDIs provided in the package 22 of the present invention have a substantially smaller standard deviation in product performance so that the MDI will typically have a consistent increased performance relative to non-overwrapped MDIs.

Table 6 further shows that the initial moisture content in parts per million for the MDIs 36 provided in the package 22 of the present invention significantly and substantially decreases while the moisture content of the control group of non-overwrapped MDIs substantially increases from the initial measurement of the moisture content.

TABLE 5

| Time point (months) | 40° C./75% RH | | 30° C./75% RH | |
|---|---|---|---|---|
| | control | wrapped | control | Wrapped |
| 0 | 6 | 6 | 6 | 6 |
| 3 | 14 | 5 | 11 | 5 |
| 4 | | | 12 | 5 |
| 6 | | | 12 | 9 |

*RSD (%) = percentage relative standard deviation based on the values for dose ex actuator obtained from 10 cans at the end of use (final nominal dose).

TABLE 6

| Time point (months) | 40° C./75% RH | | 30° C./75% RH | |
|---|---|---|---|---|
| | control | Wrapped | control | Wrapped |
| 0 | 198 | 198 | 198 | 198 |
| 3 | 751 | 50 | 412 | 61 |
| 4 | | | 408 | 83 |
| 6 | | | 521 | 30 |

Table 7 shows the loss of HFA-134a (in grams) for wrapped Albuterol 134a MDI's stored for 14 months at 30° C./60%RH and 40° C./75%RH. The data in Table 7 is a mean of 5 determinations from 3 separate batches of MDI's.

TABLE 7

| | 40° C./ 75% RH | 30° C./ 60% RH |
|---|---|---|
| Loss of HFA134a from the can (g) | 0.4 | 0.7 |
| HFA134a remaining in the pack (g) | 0.1 | 0.2 |

The results of the above mentioned tests, outlined by Tables 1–4, prove that loss in fine particulate mass (FPM) of MDIs is directly related to moisture content adjacent or within an MDI. The results tabulated in Tables 5–7 prove that variation of the content uniformity at the end life of the wrapped MDIs of the present invention is substantially less than non-wrapped MDIs. Therefore, substantial increases in product performance of MDIs 36 are possible with the package 22 of the present invention which substantially reduces or eliminates the ingression of moisture or water vapor into the enclosed volume 40. Table 7 shows proof of the operation of the virtual one way valve mechanism that permits egression of HFA-134a from package 22.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Another experiment focused on three types of foil pouches having an aluminum component providing a moisture barrier. For Foil pouches 1–3, the desiccant included calcium sulfate, silica gel, 4A molecular sieve and casein/glycerol.

Foil pouch 1 was constructed from a 9 μm aluminum foil layer. Foil pouch 1 also included a one-way valve to allow any propellant leaking from the enclosed MDI to egress from the pouch. Foil pouch 1 is available from Raackmann UK Ltd. as coextruded oriented polypropylene (20 μm), adhesive, polyester (PETP)(12 μm), adhesive, aluminum foil (9 μm), adhesive, polyethylene (60 μm).

Foil pouch 2 was constructed from a 25 μm aluminum foil layer. Foil pouch 2 is available from American National Can Company as ZANTAC® EFFERdose® Foil, Ref. DMF#1156, Polyester (PET) 0.48 mils, primer, white copolyethylene 0.50 mils, aluminum foil 1.0 mils (25 μm), copolymer 0.5 mils, linear low density polyethylene.

Foil pouch 3 was constructed from a 12.7 μm aluminum foil layer. Foil pouch 3 is available from Allusuisse/Laminated Films and Packaging (LF15015) polyester (48 gauge), adhesive, aluminum foil (0.0005 inches, 12.7 μm, adhesive, linear low density polyethylene film (4 mil). No one-way valve was present in foil pouches 2 or 3.

An MDI containing an aerosol formulation of albuterol sulfate in HFC 134a propellant was used. The desiccant used was a 10 gram silica gel pack. The control was an identical MDI without a pouch or desiccant. The moisture content was assessed initially and after 1 m and 3 m storage at 40° C./85%RH. Moisture analysis was performed using Karl Fischer Coulometric Titration. The mean results for initial and 3 m storage is shown in Table 8.

TABLE 8

Moisture Content Results for Foil Pouches 1–3 with Albuterol Sulfate/HFC 134a MDI's

| FOIL POUCH | PACKAGING | MEAN MOISTURE CONTENT (PPM) AFTER Initial | STORAGE AT 40° C./85% RH 3 months |
|---|---|---|---|
| No. 1 | control | 146 | 545 |
| No. 1 | with desiccant | 146 | 179 |
| No. 1 | without desiccant | 146 | 431 |
| No. 2 | control | 180 | 565 |
| No. 2 | with desiccant | 180 | 160 |
| No. 2 | without desiccant | 180 | 337 |
| No. 3 | control | 204 | 365 |
| No. 3 | with desiccant | 204 | 87 |
| No. 3 | without desiccant | 204 | 216 |

The results shown in table 8 clearly show that foil packaging systems with down to at least 9 μm aluminum foil are effective in reducing moisture ingress into the MDI when used in combination with a desiccant.

Foil pouch 3 from Table 8 was also evaluated using vacuum sealing and nitrogen purging in lieu of a desiccant. The results are shown in Table 9.

TABLE 9

Moisture Content Results for Vacuum Sealed and Nitrogen Purged Systems with MDI Containing Albuterol Sulfate/HFC 134a

| Moisture Protection System | Mean Moisture Content (ppm) INITITAL | after storage at 40° C./85% RH 1 MONTH | 3 MONTHS |
|---|---|---|---|
| Control | 125 | 301 | 448 |
| Nitrogen Purged Pouch | 125 | 176 | 216 |
| Vacuum Sealed Pouch | 125 | 197 | 252 |
| Foil Pouch 3 Plus Desiccant | 125 | 149 | 144 |

The results in Table 9 show that the nitrogen purging and vacuum sealing embodiments substantially reduce the rate of moisture ingress as compared to the control having no pouch. Moreover, the results demonstrate that nitrogen purging or vacuum sealing the pouch when used in combination with a desiccant could still further reduce the rate of moisture ingress.

What is claimed:

1. A drug product comprising:
  a drug formulation comprising a mixture of at least a drug and an HFA propellant;
  a fluid dispensing device including a pressurized container filled with said drug formulation; and
  a substantially moisture-impermeable polymeric film heat-shrinked onto at least a portion of the exterior of the fluid dispensing device,
  wherein the polymeric film comprises a first moisture absorbing material.

2. The drug product of claim 1 wherein the fluid dispensing device further includes a valve having a stem.

3. The drug product of claim 2 wherein the film is heat-shrinked onto the pressurized container, the valve, and the region defined by the exterior interface of the valve and stem.

4. The drug product of claim 2 wherein the film is heat-shrinked onto a portion of the pressurized container and a portion of the valve.

5. The drug product of claim 1 further including a second moisture absorbing material located within the pressurized container.

6. The drug product of claim 5 wherein the second moisture absorbing material is a second desiccant selected from the group consisting of nylon, silica gel, zeolite, alumina, bauxite, anhydrous calcium sulphate, activated bentonite clay, water absorbing clay, molecular sieve and combinations thereof.

7. The drug product of claim 6 wherein the second desiccant is contained within a sachet constructed from a nylon mesh.

8. The drug product of claim 7 wherein the sachet is loose within the pressurized container.

9. The drug product of claim 7 wherein the sachet is fixedly attached to the pressurized container.

10. The drug product of claim 6 wherein the second desiccant is in the form of granules or beads suitably large enough in size to avoid clogging a valve in the fluid dispensing device, and wherein the fluid dispensing device is a metered dose inhaler.

11. The drug product of claim 1 wherein the polymeric film is constructed from one or more polymeric layers.

12. The drug product of claim 11 wherein the one or more polymeric layers of the polymeric film are each constructed from a material selected from the group consisting of polyvinylchloride, polyvinylidenechloride, polypropylene, oriented polypropylene, polyethylene, ACLAR® and BAREX®.

13. The drug product of claim 11 wherein the film further includes one or more adhesive layers.

14. The drug product of claim 11 wherein the first moisture absorbing material is a first desiccant, and wherein at least one of said polymeric layers is impregnated, coated, treated or lined with said first desiccant.

15. The drug product of claim 14 wherein the first desiccant is selected from the group consisting of nylon, silica gel, zeolite, alumina, bauxite, anhydrous calcium sulphate, activated bentonite clay, water absorbing clay, molecular sieve and combinations thereof.

16. The drug product of claim 13 wherein one or more adhesive layers is impregnated with the first desiccant selected from the group consisting of nylon, silica gel, zeolite, alumina, bauxite, anhydrous calcium sulphate, activated bentonite clay, water absorbing clay, molecular sieve and combinations thereof.

17. The drug product of claim 1 wherein the substantially moisture-impermeable polymeric film is preformed.

18. The drug product of claim 1 wherein the drug is albuterol sulfate or a solvate thereof.

19. The drug product of claim 18 wherein the HFA propellant is 134a.

20. The drug product of claim 1 wherein the drug is fluticasone propionate or a solvate thereof.

21. The drug product of claim 1 wherein the drug is beclomethasone dipropionate or a solvate thereof.

22. The drug product of claim 1 wherein the drug is a salt, ester or solvate of salmeterol.

23. The drug product of claim 1 wherein the drug is a combination of a salt, ester or solvate of salmeterol and fluticasone propionate or a solvate thereof.

24. The drug product of claim 1 wherein the drug is a combination of a salt, ester, or solvate of salmeterol and a salt, ester or solvate of ipratropium.

25. A drug product comprising:
a drug formulation comprising a mixture of at least a drug and an HFA propellant;
a fluid dispensing means including a pressurized container filled with said drug formulation; and
a substantially moisture-impermeable polymeric film heat-shrinked onto at least a portion of the exterior of the fluid dispensing device, wherein the polymeric film comprises a first moisture absorbing material.

26. A drug product comprising:
a drug formulation comprising a mixture of at least a drug and an HFA propellant;
a fluid dispensing device including a pressurized container filled with said drug formulation and a first moisture absorbing material;
a valve having a stem; and,
a substantially moisture-impermeable polymeric film heat-shrunk into at least a portion of the exterior of the fluid dispensing device and valve stem.

27. The drug product of claim 26, wherein the first moisture absorbing material is a desiccant selected from the group consisting of nylon, silica gel, zeolite, alumina, bauxite, anhydrous calcium sulphate, activated bentonite clay, water absorbing clay, molecular sieve and combinations thereof.

28. The drug product of claim 26, wherein the first moisture absorbing material is contained within a sachet constructed from a nylon mesh.

29. The drug product of claim 26, wherein the sachet is loose within the pressurized container.

30. The drug product of claim 28, wherein the sachet is fixedly attached to the pressurized container.

31. The drug product of claim 26, wherein the first moisture absorbing material is in the form of granules or beads large in size to avoid clogging a valve in the fluid dispensing device, and wherein the fluid dispensing device is a metered dose inhaler.

32. The drug product of claim 21 wherein the substantially moisture-impermeable polymeric film is constructed from one or more polymeric films, one or more adhesive layers, and a second moisture absorbing material.

33. The drug product of claim 32 wherein the second moisture absorbing material is a desiccant, and wherein the second moisture absorbing material is located on the inner surface of the moisture-impermeable polymeric film.

34. A drug product comprising:
a drug formulation comprising a mixture of at least a drug and an HFA propellant;
a means for dispensing the drug formulation having a pressurized means containing said drug formulation and a first moisture absorbing material; and,
a heat-shrinked means for substantially preventing permeation of moisture into the dispensing means.

* * * * *